US009895862B2

(12) United States Patent
Burke et al.

(10) Patent No.: US 9,895,862 B2
(45) Date of Patent: Feb. 20, 2018

(54) MULTI-LAYERED ASSEMBLY WITH TIGHT PEEL CONTROL

(71) Applicant: Argotec LLC, Greenfield, MA (US)

(72) Inventors: Thomas C. Burke, Conway, MA (US); Jeffrey James O'Brien, Sunderland, MA (US); Viktor Vlasenko, Greenfield, MA (US)

(73) Assignee: Schweitzer-Mauduit International, Inc., Alpharetta, GA (US)

(*) Notice: Subject to any disclaimer, the term of this patent is extended or adjusted under 35 U.S.C. 154(b) by 0 days.

(21) Appl. No.: 14/265,051

(22) Filed: Apr. 29, 2014

(65) Prior Publication Data

US 2014/0349053 A1    Nov. 27, 2014

Related U.S. Application Data

(60) Provisional application No. 61/816,836, filed on Apr. 29, 2013.

(51) Int. Cl.
*B32B 7/12*    (2006.01)
*C08F 8/44*    (2006.01)
(Continued)

(52) U.S. Cl.
CPC ............ *B32B 7/12* (2013.01); *A61F 13/0259* (2013.01); *A61L 15/26* (2013.01); *B32B 27/08* (2013.01); *B32B 27/40* (2013.01); *B32B 33/00* (2013.01); *C08F 8/44* (2013.01); *C09J 7/0207* (2013.01); *C09J 7/0296* (2013.01); *C09J 175/04* (2013.01); *B32B 2250/02* (2013.01); *B32B 2250/24* (2013.01); *B32B 2255/10* (2013.01);
(Continued)

(58) Field of Classification Search
None
See application file for complete search history.

(56) References Cited

U.S. PATENT DOCUMENTS 5,088,483 A    2/1992  Hainecke
5,738,642 A *  4/1998  Heinecke et al. .............. 602/58
(Continued)

FOREIGN PATENT DOCUMENTS

EP    1002016 B1      2/2005
JP    2006021354 A    1/2006
WO    WO 99/07786  *  8/1998  .............. C08L 23/08

OTHER PUBLICATIONS

MacKnight, et al., "Properties of Ethylene-Methacrylic Acid Copolymers and Their Sodium Salts: Infrared Studies", J. Phys. Chem., 1968, 72, pgs. 1122-1126.*
(Continued)

*Primary Examiner* — Alexandre F Ferre
*Assistant Examiner* — Elaine M Vazquez
(74) *Attorney, Agent, or Firm* — Reza Mollaaghababa; Thomas Engellenner; Pepper Hamilton LLP

(57) ABSTRACT

Embodiments disclosed herein provide for multi-layered assemblies comprising a carrier having opposed sides; a heat sealable layer disposed on at least a portion of one of said sides of the carrier, said heat sealable layer comprising a partially salt neutralized ionomer; and a polymeric film comprising polyurethane and having opposed sides, wherein one of said sides of the polymeric film is in at least partial contact with said heat sealable layer, methods of making the same as well as other variations.

17 Claims, 11 Drawing Sheets

(51) Int. Cl.

| | | |
|---|---|---|
| | *C09J 7/02* | (2006.01) |
| | *B32B 33/00* | (2006.01) |
| | *C09J 175/04* | (2006.01) |
| | *A61F 13/02* | (2006.01) |
| | *B32B 27/08* | (2006.01) |
| | *A61L 15/26* | (2006.01) |
| | *B32B 27/40* | (2006.01) |

(52) U.S. Cl.
CPC ....... *B32B 2307/31* (2013.01); *B32B 2333/00* (2013.01); *B32B 2375/00* (2013.01); *B32B 2535/00* (2013.01); *B32B 2556/00* (2013.01); *C09J 2433/001* (2013.01); *C09J 2475/00* (2013.01); *Y10T 428/1452* (2015.01); *Y10T 428/2826* (2015.01); *Y10T 428/31573* (2015.04)

(56) References Cited

U.S. PATENT DOCUMENTS

2005/0139505 A1 6/2005 Miller
2008/0280037 A1* 11/2008 Sheridan et al. .......... 427/208.8

OTHER PUBLICATIONS

Lubrizol, Estane 58309 TPU Product Sheet.*
PCT Notification of Transmittal of the International Search Report and the Written Opinion of the International Searching Authority, or the Declaration, PCT/US2014/035912, dated Nov. 18, 2014 (10 pages).
Examination Report received in AU Application No. 2014260016 dated Jan. 23, 2017; 2 pages.
Office Action received in CN Application No. 201480037325.5 dated Apr. 12, 2017; 11 pages.

* cited by examiner

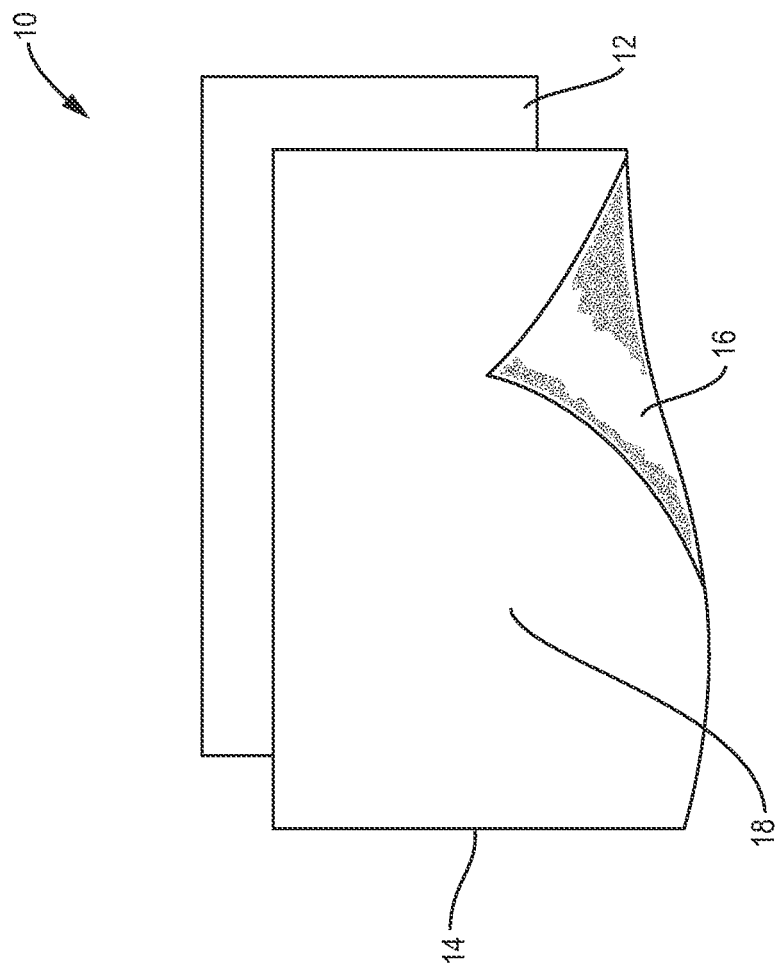

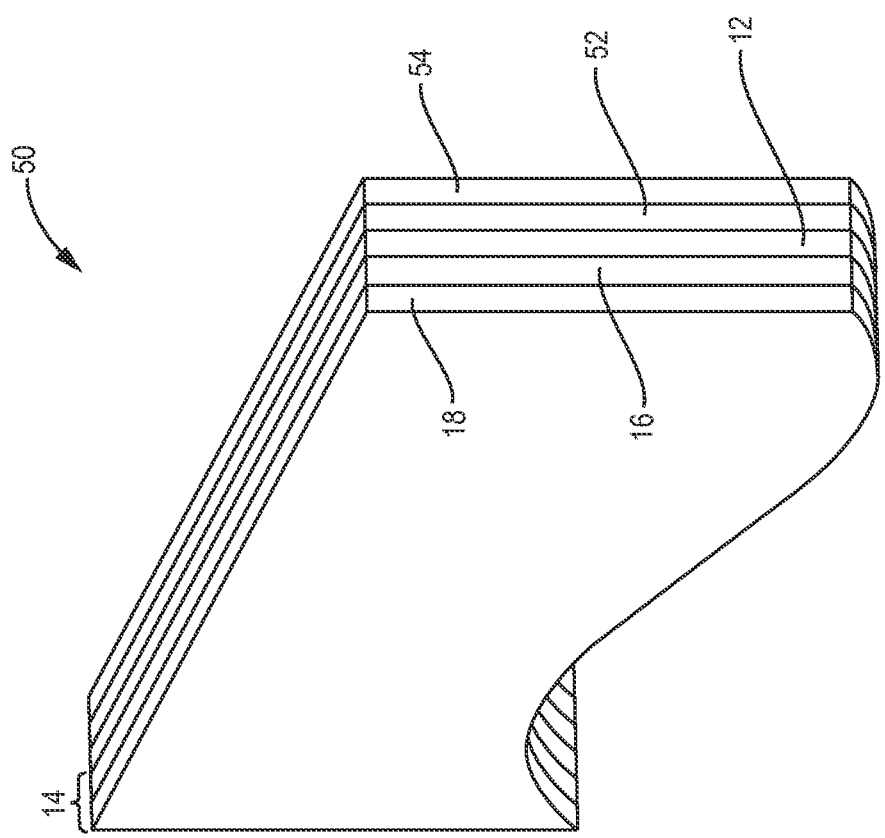

AVERAGE FORCE VS. DISTANCE ALONG ROLL LENGTH (g/in)

| DISTANCE ACROSS WEB → | 8 in | 14 in | 20 in | 26 in | 32 in | 38 in | 44 in | 50 in | AVERAGE | TD STD. DEVIATION |
|---|---|---|---|---|---|---|---|---|---|---|
| DISTANCE ALONG ROLL LENGTH (feet) 1 | 149 | 123 | 142 | 162 | 156 | 152 | 161 | 160 | 151 | 13.1 |
| 5 | 139 | 129 | 144 | 152 | 129 | 120 | 134 | 155 | 138 | 12.1 |
| 10 | 144 | 123 | 140 | 159 | 153 | 120 | 141 | 162 | 143 | 15.4 |
| 15 | 146 | 153 | 133 | 144 | 127 | 112 | 144 | 156 | 139 | 14.6 |
| 20 | 145 | 123 | 132 | 151 | 140 | 129 | 145 | 140 | 138 | 9.4 |
| 25 | 158 | 137 | 140 | 139 | 131 | 128 | 155 | 158 | 143 | 12.1 |
| 30 | 144 | 131 | 139 | 147 | 138 | 119 | 156 | 157 | 141 | 12.7 |
| 35 | 131 | 129 | 142 | 149 | 150 | 127 | 136 | 164 | 141 | 12.8 |
| 2000 | 148 | 124 | 146 | 156 | 141 | 115 | 156 | 130 | 140 | 15.1 |
| 2005 | 134 | 123 | 127 | 133 | 159 | 114 | 136 | 136 | 133 | 13 |
| 2010 | 133 | 122 | 131 | 141 | 122 | 109 | 140 | 139 | 130 | 11.2 |
| 2015 | 140 | 126 | 110 | 129 | 125 | 113 | 135 | 130 | 126 | 10.2 |
| 2020 | 135 | 123 | 124 | 138 | 121 | 109 | 131 | 135 | 127 | 9.3 |
| 2025 | 128 | 110 | 125 | 143 | 124 | 135 | 134 | 137 | 130 | 10.2 |
| 2030 | 138 | 124 | 120 | 137 | 115 | 120 | 128 | 151 | 129 | 12 |
| AVERAGE (g/in) | 141 | 127 | 133 | 145 | 135 | 121 | 142 | 147 | 137 | GRAND AVG. |
| MD STD. DEV. (g/in) | 8.0 | 9.3 | 10.2 | 9.6 | 14.0 | 11.4 | 10.4 | 12.3 | 13.5 | Overall Std.Dev. |

FIG. 4

PEEL STRENGTH AFTER 24 HOURS AGED AT 120° F

| Distance Across Roll (in) | 3 in | 9 in | 15 in | 21 in | 27 in | 33 in | 39 in | 45 in | 51 in | 57 in | Average | Std. Dev. | 3x Std Dev as % of Avg |
|---|---|---|---|---|---|---|---|---|---|---|---|---|---|
| Peel Strength (g/in) | 152 | 214 | 172 | 175 | 219 | 215 | 191 | 175 | 219 | 193 | 192.4 | 22.5 | 35% |

FIG. 5

MULTI-LAYERED ASSEMBLY WITH TIGHT PEEL CONTROL

CROSS-REFERENCE TO RELATED APPLICATIONS

This application claims priority to U.S. Provisional Application No. 61/816,836, filed Apr. 29, 2013, which is hereby incorporated by reference in its entirety.

FIELD OF THE INVENTION

The present disclosure relates to urethane based polymer films having release liners that exhibit improved peel control over a range of peel values.

BACKGROUND OF THE INVENTION

Polymer films used, e.g., in medical dressings and drapes, referred to as dressings below, are conformable, i.e., the films are extremely thin, flexible and supple. They are typically supplied with a protective release liner, which covers a pressure sensitive adhesive layer coated surface of the film. When the protective release liner is removed, the adhesive coated film tends to wrinkle and adhere to itself, thereby interfering with the smooth, aseptic application of the dressing to, e.g., a patient's skin. Various delivery systems have been proposed to address this problem, wherein such delivery systems include a carrier which is applied to a side of the polymer film which is oppositely situated to the side of the polymer film to which the pressure sensitive adhesive layer is applied.

However, despite the improvement that such carriers have provided, such carriers are not able to maintain the integrity of the peel force between a carrier and a polymeric film.

The ability to apply a polymer film without creasing or wrinkling depends in large part on the peel force. It will be understood that control over the bonds produced during a heat seal portion of manufacturing can be affected by a number of variables including the materials heat sealed, the temperature of a heated roll, the speed of a web and the pressure between a heated roll and a nip roll. Furthermore, it will be understood that sterilization of the resulting products can also affect the bond strength. In particular, it is known that the strength of the bond between a backing adhesive and a patient's skin can be affected by gamma, electron beam or ethylene oxide sterilization. By way of example, ethylene oxide sterilization can in many medical dressing structures cause bond strength issues. For example, it can increase the strength of the bond between a urethane film and a heat sealed surface, which couples the film to a carrier, to such a high level that would make removing the film from the carrier impractical. Exposure to wide temperature fluctuations during transportation also affects the bond strength.

Accordingly, there is a need for an assembly that can substantially maintain the peel strength between a carrier and a polymeric film during assembly, sterilization, packaging, shipping, and storage of the assembly.

SUMMARY OF THE INVENTION

The present teachings are generally directed to a multi-layered assembly that includes a heat sealable layer that provides a non-permanent bond between a carrier and a polyurethane film. As discussed in more detail below, the heat sealable layer, which comprises a partially salt neutralized ionomer, can provide a releasable bond between the carrier and the polyurethane film characterized by a peel force between about 50 grams/inch to about 600 grams/inch. One advantage of a multi-layered assembly according to the present teachings is that in many embodiments the peel force can vary by less than 25% when the temperature of the assembly is raised from room temperature (e.g., 25° C.) to about 55-65° C. Another advantage of a multi-layered assembly according to the present teachings is that in many embodiments the peel force can vary by less than 25% when the assembly is subjected to ethylene oxide sterilization and can vary by less than 10% when the assembly is subjected to gamma ray sterilization. Yet, another advantage of a multi-layered assembly according to the present teachings is that in many embodiments the peel force remains below a threshold, e.g., 400 grams/inch, as the temperature of the assembly is varied over a range of about 80° C. to about 190° C.

In some embodiments, a multi-layered assembly according to the present teachings can include a conformable polyurethane film and a removable carrier attached to the conformable film via a heat sealable layer, wherein the heat sealable layer is non-permanently heat sealed to the conformable film. In some embodiments, the heat sealable layer comprises a partially neutralized acrylic acid based polymer, such as partially neutralized ethylene acrylic acid. In some embodiments, the acrylic acid based polymer comprises a partial neutralization of from about 10% to about 35%.

In some embodiments, the multi-layered assembly has an improved peel force between the polymeric film and the heat sealable layer. In some embodiments, the improved peel force is marked by the assembly's ability to maintain a relative constant peel force of about 200 grams/inch over an uninterrupted period of 24 hours at 50° Celsius.

In some embodiments, the multi-layered assembly may further comprise at least one of a pressure sensitive adhesive layer attached to a side of the polyurethane film oppositely situated from the heat sealable layer, a protective release liner disposed on the pressure sensitive adhesive layer and/or the film, and a release liner disposed on the carrier opposite to the heat sealable layer. The multi-layered assembly may additionally or alternatively comprise a release agent disposed on a side of the carrier opposite to the heat sealable layer.

In some embodiments, a method of manufacturing an adhesive composite dressing according to the present teachings is provided, where the method comprises (a) providing a conformable film having top and bottom sides; (b) providing a carrier having a heat sealable layer formed on a bottom side of the carrier and (c) non-permanently heat sealing the bottom side of the carrier to the top side of the film via the heat sealable layer. In some embodiments, the heat sealable layer can be formed on the bottom side of the carrier, e.g., by emulsion coating, extrusion coating, or as an extruded layer. In some embodiments, the carrier and the heat sealable layer may optionally include a cut defining a window proximate a center of the carrier that, when removed, forms a window in the frame dressing.

In some embodiments, the multi-layered assemblies described herein can extend the range of temperatures that the assembly can be exposed to and continue to exhibit an improved, narrow range of peel values. Other advantages are also readily apparent in view of the embodiments disclosed herein.

In one aspect, a multi-layered assembly is disclosed, which includes a carrier having opposed sides, a heat sealable layer disposed on at least a portion of one of said sides of the carrier, where the heat sealable layer comprises a partially salt neutralized ionomer. The multi-layered assembly further includes a polymeric film comprising polyurethane and having opposed sides, where one of said sides of the polymeric film is in at least partial contact with said heat sealable layer.

In some embodiments, the partially salt neutralized ionomer constitutes at least 50%, or at least 60%, or at least 70%, or at least 80%, or at least 90%, or 100% of the heat sealable layer. In some embodiments, the polyurethane constitutes at least 50%, or at least 60%, or at least 70%, or at least 80%, or at least 90%, or 100% of the polymeric film. The polyurethane can be any of an aromatic polyether urethane, polyether urethane, or poly (ether ester) block copolymers and tripolymers. In some embodiments, the heat sealable layer has a thickness in a range of about 2 micrometers (microns) to about 100 microns.

In some embodiments, the partially salt neutralized ionomer exhibits a salt neutralization level in a range of 5% to 70%, or 20% to 40%, e.g., 30%. In some embodiments, the salt includes any of a sodium, a potassium, a magnesium, calcium, or a zinc salt, or a combination thereof.

In some embodiments, the partially salt neutralized ionomer includes a partially salt neutralized ethylene acrylic acid copolymer. In some embodiments, the partially salt neutralized ethylene acrylic acid copolymer exhibits a salt neutralization level in a range of 20% to 40%, e.g., 30%. For example, the salt can be sodium carboxylate.

In some embodiments, the heat sealable layer exhibits, when disposed on said carrier and in absence of said polymer film, an FTIR (Fourier Transform Infrared) spectrum exhibiting a peak at about 1700 cm$^{-1}$ and a peak in a range of about 1500 to about 1560 cm$^{-1}$. A ratio of the height of the peak at about 1700 cm$^{-1}$ to the height of the peak in the range of about 1500 to about 1560 cm$^{-1}$ is in a range from about 20 to about 0.5, e.g. about 10 to about 1. When the heat sealable layer includes a sodium neutralized ionomer the FTIR spectrum exhibits a peak at about 1700 cm$^{-1}$ and a peak at about 1545 cm$^{-1}$ with the ratio of the height of the peak at 1700 cm$^{-1}$ and the peak at 1545 cm$^{-1}$ in a range of about 10 to 1. However, if other salts are used a different peak would be measured and would be readily apparent to one of skill in the art.

In some embodiments, the polymeric film is releasably sealed to the carrier via said heat sealable layer such that a peel force in a range of about 50 grams/inch to about 600 grams/inch is required to release the polymeric film. Unless otherwise stated, the peel force values disclosed herein refer to a peel force required to release the polymeric film when the assembly is at room temperature (i.e., at a temperature of about 25° C.). The peel force can be determined where the peel angle is 90 degrees and/or the film is removed at a rate of about 10 to about 300 inches per minute. In some embodiments, the peel force varies by less than 25% when temperature is raised from room temperature to about 50° Celsius. Further, in some embodiments, the peel force varies by less than 25% after said assembly is subjected to ethylene oxide sterilization. In some embodiments, the peel force varies by less than 10% after said assembly is subjected to gamma ray sterilization. In some embodiments, the peel force is less than about 600 grams/inch after the multi-layered assembly is exposed to a temperature of about 50° C. for about 24 hours.

In some embodiments, the polymeric film comprises a pressure sensitive adhesive layer disposed on a side thereof opposed to the side that is in at least partial contact with said heat sealable layer. In some embodiments, the multi-layered assembly further comprises a protective release liner disposed on the pressure sensitive adhesive layer.

In a related aspect, a collection of multi-layered assemblies is disclosed, which comprises a plurality of multi-layered assemblies. Each of the multi-layered assemblies comprises a carrier having opposed sides, a heat sealable layer disposed on at least a portion of one of said sides of the carrier, where the heat sealable layer comprises a partially salt neutralized ionomer. Further, each of the multi-layered assemblies includes a polymeric film comprising polyurethane and having opposed sides, where one of said sides of the polymeric film is in at least partial contact with the heat sealable layer. In some embodiments, the variation in peel force as measured by 3 times the standard deviation as a percent of the average peel force is less than 30%. In some embodiments, the polymeric film comprises a pressure sensitive adhesive layer disposed on a side thereof opposed to the side that is in at least partial contact with the heat sealable layer. Further, in some embodiments, each multi-layered assembly comprises a protective release liner disposed on the pressure sensitive adhesive layer. In some embodiments, each of the multi-layered assemblies can exhibit the characteristics discussed above.

In a related aspect, a multi-layered assembly is disclosed, which includes a carrier having opposed sides, a heat sealable layer disposed on at least a portion of one of said sides of the carrier, and a polymeric film comprising a polyurethane and having opposed sides, where one of said sides of the polymeric film is in at least partial contact with the heat sealable layer. The polymeric film is releasably sealed to the carrier via the heat sealable layer such that a peel force in a range of about 50 grams/inch to about 600 grams/inch is required to release the polymeric film.

The peel force varies by less than about 50 grams/inch when the assembly is heated to a temperature of about 50° C. for up to about 24 hours. In some embodiments, the peel force is in a range of about 200 grams/inch to about 500 grams/inch. In some embodiments, the peel force is in a range of about 200 grams/inch to about 400 grams/inch. In some embodiments, the polyurethane comprises any of an aromatic polyether urethane, polyether urethane, or poly (ether ester) block copolymers and block tripolymers.

In a related aspect, a multi-layered assembly is disclosed, which includes a carrier having opposed sides, a heat sealable layer disposed on at least a portion of one of said sides of the carrier, and a polymeric film comprising polyurethane and having opposed sides, where one of said sides of the polymeric film is at least in partial contact with the heat sealable layer. The polymeric film is releasably sealed to said carrier via said heat sealable layer such that a peel force required to release the polymeric film remains below 400 grams/inch as the temperature of the assembly varies from about 25° to about 50° C. The heat sealable layer can include a partially salt neutralized ionomer. In some embodiments, the partially salt neutralized ionomer can be a partially salt neutralized ethylene acrylic acid copolymer. In some embodiments, the level of salt neutralization can be in a range of 5% to 70%.

In another aspect, a method for fabricating a multi-layered assembly is disclosed, which includes coating a surface of a carrier with a partially salt neutralized ionomer emulsion, casting a polyurethane resin on said coated surface of the carrier, and exposing said polyurethane and ionomer coated carrier to an elevated temperature to form a releasable bond between the polyurethane and the carrier. In some embodiments, the elevated temperature is in a range of about 80° C. to about 190° C. In some embodiments, the carrier can be any of a kraft paper, polyester, polyolefin, or polylactic acid film. In some embodiments, the ionomer emulsion is a partially sodium neutralized ethylene methacrylic acid emulsion. In some embodiments, an FTIR spectrum of the ionomer emulsion exhibits a peak at 1700 cm$^{-1}$ and a peak at about 1500 to about 1560 cm$^{-1}$, where a ratio of the height of the peak at 1700 cm$^{-1}$ to the height of the peak at about 1500 to about 1560 cm$^{-1}$ is in a range of about 20 to 0.5, e.g. 6 to 1.

BRIEF DESCRIPTION OF THE DRAWINGS

FIG. 1 is an example of a schematic depicting an exemplary multi-layered assembly.

FIG. 2A is an example of a schematic depicting another exemplary multi-layered assembly.

FIG. 4 is a compilation of data obtained from the multi-layered assembly formed from Example 1, wherein the data shows a 3× standard deviation as a percent of average peel of about 29.6% after heat aging at 120 degrees Fahrenheit for 24 hours.

FIG. 5 is a table depicting further data obtained from an exemplary multi-layered assembly.

DETAILED DESCRIPTION

Figure 1A:
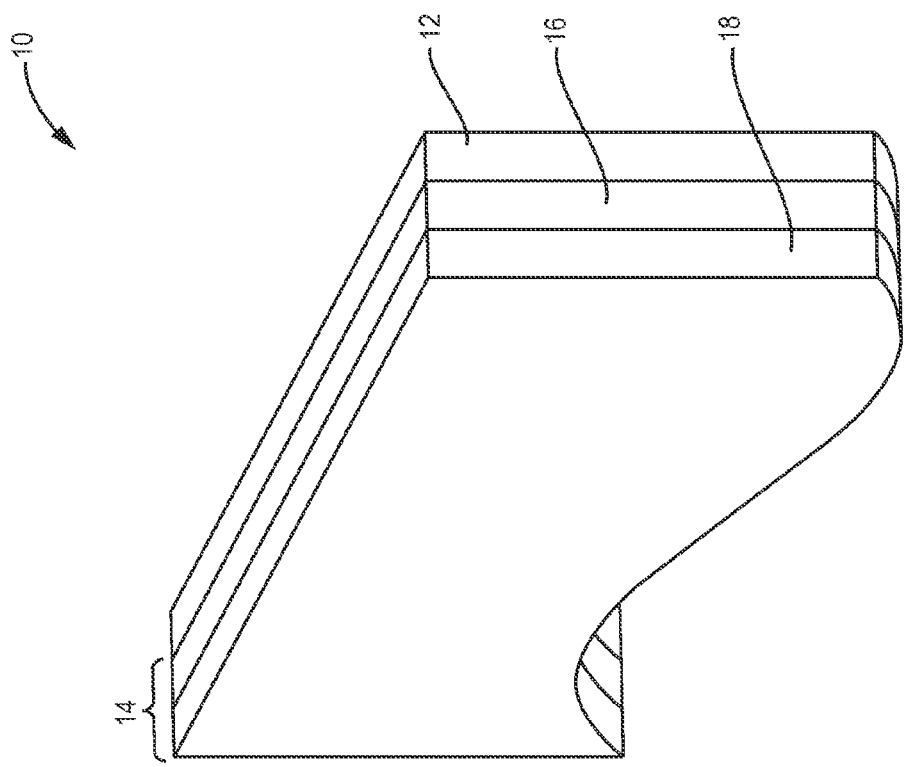
FIG. 1A is another example of a schematic depicting an exemplary multi-layered assembly.

In some embodiments, a multi-layered assembly is disclosed that provides a carrier delivered polyurethane polymeric film. The assembly can comprise a heat sealable layer disposed between the carrier and the polymeric film. In some embodiments, the heat sealable layer is applied to a bottom side of the carrier as an emulsion coating, an extrusion coating, an extrusion layer, and the like. In some embodiments, the heat sealable layer may be non-permanently heat sealed to a top side of the polymeric film to create an assembly in which the polymeric film can be removed from the carrier via a peel force in a range of about 50 grams/inch to about 600 grams/inch, e.g., a peel force of about 200 grams/inch. In some embodiments, the peel force required to remove the polyurethane polymeric layer varies by less than 25% when the assembly is maintained at a temperature of about 50 C for up to 24 hours.

The term "about" as used herein denotes a variation of at most 5%.

As used herein and throughout, the "peel force" refers to a force in grams per inch required to remove the heat sealable layer from the polymeric film at a tear angle of about 90 degrees with the assembly at room temperature (i.e. 25 C) and a peel rate of about 10 to about 300 inches per minute. The term "lock seal", which can also be referred to as a "destruct seal," refers to a seal where the peel force required to remove the heat sealable layer tears or rips the layer. The "lock seal" may require a force of greater than 700 grams/inch to remove the layer.

In some embodiments, the heat sealable layer comprises an acrylic acid based polymer. In some embodiments, the acrylic acid based polymer is an ethylene acrylic acid based polymer. In some embodiments, the acrylic acid based polymer has been partially neutralized within a range to allow removing the polymeric layer from the carrier via a peel force less than a threshold value, e.g., less than about 600 grams/inch. As discussed in more detail below, it has been unexpectedly discovered that the peel force for removing the polymeric film from the carrier in a multi-layered assembly according to the present teachings shows a low variability over a wide range of temperatures and exposure time.

In some embodiments, the assembly may further comprise a release agent disposed on a top side of the carrier, oppositely situated to the heat sealable layer. Without being bound to any particular theory, such a release agent can be used to facilitate the rolling out of the assembly when the assembly is in a roll or a sheeted configuration by preventing the polymeric film from sticking to the carrier. In some embodiments, the assembly may further comprise a pressure sensitive adhesive layer coated on a bottom side of the polymeric film and a protective release liner disposed on the pressure sensitive adhesive layer.

Embodiments disclosed herein also provide an adhesive composite dressing comprising: a conformable film having top and bottom sides; a carrier having top and bottom sides; and a heat sealable layer disposed on the bottom side of the carrier, wherein the heat sealable layer facilitates heat sealing of the carrier to the top side of the conformable film, and can, for example, improve the integrity and constancy of the controlled peel force of the assembly. The assembly may also further comprise a release agent, such as, e.g., a release liner disposed on a side of the carrier opposite to the heat sealable layer, a pressure sensitive adhesive layer coated on at least a portion of the bottom side of the conformable film, and a protective release liner releasably adhered to the pressure sensitive adhesive layer opposite the conformable film.

In some embodiments, a multi-layered assembly according to the present teachings comprises a carrier having opposed sides; a heat sealable layer disposed on at least a portion of one of said sides of the carrier, said heat sealable layer comprising a partially salt neutralized ionomer; and a polymeric film comprising polyurethane and having opposed sides, wherein one of said sides of the polymeric film is in at least partial contact with said heat sealable layer.

As used herein, the term "partially salt neutralized ionomer" refers to an ionomer where a fraction of the ionized groups of the ionomer are neutralized by the addition of a salt. In some embodiments, the salt is a sodium, a potassium, a magnesium, calcium, or a zinc salt, or a combination thereof. In some embodiments, the partially salt neutralized ionomer comprises a partially salt neutralized ethylene acrylic acid copolymer. In some embodiments, the ionomer is ethylene methacrylic (EMAA) polymer. In some embodiments, the ionomer is ethylene ethyl acrylic acid (EAA) polymer.

In some embodiments, the ionomer exhibits a salt neutralization level (i.e., the fraction of the ionized groups that are neutralized) in a range of about 5 to about 70%, about 5 to about 60%, about 5 to about 50%, about 5 to about 40%, about 5 to about 35%, about 5 to about 30%, about 10 to about 70%, about 10 to about 60%, about 10 to about 50%, about 10 to about 40%, about 10 to about 35%, about 10 to about 30%, about 20 to about 70%, about 20 to about 60%, about 20 to about 50%, about 20 to about 40%, about 20 to about 35%, about 20 to about 30%, about 25 to about 70%, about 25 to about 60%, about 25 to about 50%, about 25 to about 40%, about 25 to about 35%, about 25 to about 30%, about 30 to about 70%, about 30 to about 60%, about 30 to about 50%, about 30 to about 40%, about 30 to about 35%, about 40 to about 70%, about 40 to about 60%, about 40 to about 50%, about 50 to about 60%, about 50 to about 70%, or about 60 to about 70%. In some embodiments, the ionomer exhibits a salt neutralization level of about 5, 10, 15, 20, 25, 30, 35, 40, 45, 50, 55, 60, 65, or 70%.

Salt neutralization can also be measured by FTIR (Fourier Transform Infrared) analysis of the multi-layered assembly. In some embodiments, FTIR spectrum of the heat sealable layer disposed on the carrier can be obtained, in absence of the polymer layer, to determine the salt neutralization level. For example, the ratio of the heights of the peaks of such an FTIR spectrum at about 1700 $cm^{-1}$ and a peak in the range of about 1500 to 1560 $cm^{-1}$ can be used to provide a measure of the level of salt neutralization of the heat sealable layer. Depending upon the salt used for the neutralization, the peak at the lower wave number can vary within the range of about 1500 to 1560 $cm^{-1}$. For example, a sodium salt partially neutralized layer will show a peak at about 1545 $cm^{-1}$ and can be used to provide a measure of the level of salt neutralization of the heat sealable layer. In some embodiments, this ratio of the heights of the two peaks can be in a range of about 4 to about 1, or about 5 to about 1, or about 5.1 to about 1, or about 5.2 to about 1, or about 5.3 to about 1, or about 5.4 to about 1, or about 5.5 to about 1, or about 5.6 to about 1, or about 5.7 to about 1, or about 5.8 to about 1, or about 5.9 to about 1, or about 6 to about 1. In some embodiments, the ratio is about 4.6 to about 1 or about 5.6 to about 1. In some embodiments, the ratio of the two peaks is about 15 to about 1, about 14 to about 1, about 13 to about 1, about 12 to about 1, about 11 to about 1, about 10 to about 1, about 9 to about 1, about 8 to about 1, or about 7 to about 1. In some embodiments, the ratio is about 20 to about 0.5. In some embodiments, the ratio is anywhere from about 6 to about 1. In some embodiments, the level of salt neutralization of the heat sealable layer can, be monitored by using FTIR during manufacturing to achieve a desired level characterized by a ratio of the heights of the aforementioned peaks of the FTIR spectrum of the heat sealable layer.

In some embodiments of the multi-layered assemblies disclosed herein, the polymeric film comprises a pressure sensitive adhesive layer disposed on a side thereof opposed to the side that is in at least in partial, or complete, contact with said heat sealable layer. In some embodiments, the multi-layered assemblies further comprise a protective release liner disposed on the pressure sensitive adhesive layer.

In some embodiments, the polyurethane layer of the multi-layered assembly comprises an aromatic polyether urethane. In some embodiments, the polyurethane layer comprises an aliphatic polyurethane, polyether urethane, or poly (ether ester) block copolymers and block tripolymers.

In some embodiments, the polymeric film is releasably sealed to the carrier via the heat sealable layer. As used herein, the phrase "releasably sealed" refers to a seal between two layers that is not a permanent or locked seal. That is, the seal can be broken by application of a moderate amount of force (e.g., a lateral force in a range of about 50 grams/inch to about 600 grams/inch). In some embodiments, the amount of force required to release the polymeric film in a multi-layered assembly according to the present teachings that is releasably sealed via the heat sealable layer to the carrier is in a range of about 50 grams/inch to about 600 grams/inch, or about 50 grams/inch to about 500 grams/inch, or about 50 grams/inch to about 400 grams/inch, or about 50 grams/inch to about 300 grams/inch, or about 50 grams/inch to about 200 grams/inch, or about 50 grams/inch to about 100 grams/inch. In some embodiments, the amount of force to release the polymeric film that is releasably sealed is about 50, 100, 150, 200, 250, 300, 400, 500, or 600 grams/inch. In some embodiments, the amount of force to release the polymeric film that is releasably sealed is less than 600, 500, 400, 300, 200, 100, or 75 grams/inch. Further the peal force to remove the polymeric film does not rip or tear the film.

One unexpected advantage, which could not have been predicted, of the presently described multi-layered assemblies is that the peel force required to release the polymeric film from the carrier does not vary by a significant amount when the assembly is exposed to a wide range of temperatures or different sterilization conditions. This is in contrast to prior assemblies where the peel force would increase significantly when exposed to heat or sterilization conditions, which would make them impractical for certain uses. Therefore, in some embodiments of the multi-layered assemblies, the peel force varies by less than 25% when the temperature of the assemblies is varied over a range from about room temperature to about 50° C. In some embodiments, the peel force varies by less than 20, 15, 10, or 5% when the assembly is exposed to elevated temperatures in the above ranges. In some embodiments, the peel force varies by less than about 25%, 20%, 15%, 10%, or 5% when the temperature of the assembly is increased from room temperature to about 50° C. In some embodiments, the peel force exhibits such variations when the assemblies according to the present teachings are exposed to the aforementioned temperatures for a time period up to about 24 hours.

In some embodiments, the peel force varies by less than 25%, 20%, 15%, 10%, or 5% after the assembly is subjected to ethylene oxide sterilization. In some embodiments, the peel force varies by less than 25%, 20%, 15%, 10%, or 5% after the assembly is subjected to gamma ray sterilization. In some embodiments, the amount of gamma rays that the assembly or layers are exposed to is up to 20, 30, or 40 kilograys.

In some embodiments, the peel force required to release the polymeric film from the carrier (i.e., to break the bonds generated by the heat sealable layer between the polyurethane film and the carrier) is less than that of a lock seal. This is, the peel force is less than about 700 grams/inch, and in some embodiments, less than about 600 grams/inch. In some embodiments, the peel force is less than about 600, 500, 450, or 400 grams/inch after the multi-layer assembly is exposed to a temperature of about 50° C. for up to about 24 hours. In some embodiments, the peel force is about 200 to about 450, about 200 to about 400, about 200 to about 350, about 200 to about 300 grams/inch after the multi-layer assembly is exposed to a temperature about 50° C. for about 4, 8, 12, 16, 20, or 24 hours.

In some embodiments, a collection of multi-layered assemblies, comprising a plurality of multi-layered assemblies is provided, wherein each of the multi-layered assemblies comprises a carrier having opposed sides, a heat sealable layer disposed on at least a portion of one of said sides of the carrier, said heat sealable layer comprising a partially salt neutralized ionomer, and a polymeric film comprising polyurethane and having opposed sides, wherein one of said sides of the polymeric film is in at least partial contact with said heat sealable layer, wherein the variation in peel force as measured by 3 times the standard deviation as a percent of the average peel force is less than 30%. Each of the plurality of the multi-layered assemblies can also have elements and characteristics as described herein for the multi-layered assemblies.

In some embodiments, a multi-layered assembly is provided, wherein the multi-layered assembly comprises a carrier having opposed sides, a heat sealable layer disposed on at least a portion of one of said sides of the carrier, a polymeric film comprising a polyurethane and having opposed sides, wherein one of said sides of the polymeric film is at least in partial contact with said heat sealable layer, wherein said polymeric film is releasably sealed to said carrier via said heat sealable layer such that a peel force in a range of about 50 grams/inch to about 500 grams/inch is required to release the polymeric film, and wherein said peel force varies by less than 50 g/inch when temperature of said assembly is exposed to a temperature of 50° C. for up to 24 hours.

Methods of preparing, or making, multi-layered assemblies according to the present teachings are also provided. Although embodiments disclosed herein can be used to prepare the multi-layered assemblies, any suitable method can be used. In some embodiments, the method comprises coating a surface of a carrier with a partially salt (e.g., sodium salt) neutralized ionomer, e.g., by emulsion coating or extrusion coating. A polyurethane polymeric film can be cast on the partially salt neutralized ionomer disposed on the carrier to form a multi-layered assembly according to the present teachings. In some embodiments, the carrier is kraft paper. In some embodiments, the carrier is a polymer film. In some embodiments, the polymer film is a polyester, polyolefin, or polylactic acid film. Examples of polymer films, include, but are not limited to, PET (polyethylene terephthalate), PP (polypropylene), PE (polyethylene), PS (polystyrene), or nylon.

In some embodiments, the ionomer is a partially sodium neutralized ethylene methacrylic acid emulsion. In some embodiments, the emulsion has a FTIR spectrum characterized by a peak at about 1700 cm$^{-1}$ and another peak in the range of about 1500 to about 1560 cm$^{-1}$, where peak height ratio of the peak at the higher wavenumber relative to the peak at the lower wavenumber is in a range about 6 to 1, 10 to 1, 20 to 0.5 or any range or specific ratio disclosed herein. In some embodiments, the peak in the range of about 1500 to about 1560 cm$^{-1}$ is at about 1545 cm$^{-1}$. For example, in some embodiments, the peak for a sodium neutralized ionomer will be at about 1545 cm$^{-1}$.

The multi-layered assemblies described herein can also be useful in connection with any conformable film having a pressure-sensitive adhesive coating on it. In some embodiments, the preferred conformable film materials are translucent or transparent polymeric films (e.g., films comprising polyurethane). In some embodiments, the film is preferably conformable to anatomical surfaces. As such, when the film is applied to an anatomical surface, it can, for example, conform to the surface even when the surface is moved. In some embodiments, the film is also conformable to animal anatomical joints such that when the joint is flexed and then returned to its unflexed position, the film stretches to accommodate the flexure of the joint, but is resilient enough to continue to conform to the joint when the joint is returned to its unflexed condition. Non-limiting examples of characteristics of films that can be used with the assemblies described can be found in, for example, U.S. Pat. Nos. 5,088,483 and 5,160,315, the disclosures of which are hereby incorporated by reference in their entirety.

In some embodiments, the film includes, but is not limited to, an elastomeric polyurethane, a polyether-ester copolymer, such as, e.g., a hytrel elastomer, Pebax, polyether block amide films, and the like. In some embodiments, the film is an aromatic polyether urethane film. These films combine the properties of resiliency, high moisture vapor permeability, and transparency found in backings that can be used in the assemblies described herein. In some embodiments, the pressure sensitive adhesive layer may comprise those adhesives that are typically applied to the skin, such as, but not limited to, acrylic acid copolymers described in U.S. Pat. No. RE 24,906, the disclosure of which is hereby incorporated by reference, including, but not limited to, 97:3 isooctyl acrylic acid:acrylamide copolymer. In some embodiments, the polymer is a 70:15:15 isooctyl acrylate: ethyleneoxide acrylate: acrylic acid terpolymer, as described in U.S. Pat. No. 4,373,410 (Example 31), the disclosure of which is hereby incorporated by reference in its entirety. Other adhesives that can be used are described in U.S. Pat. Nos. 3,389,827, 4,112,213, 4,310,509, and 4,323,557, the disclosures of which are hereby incorporated by reference in their entirety. Inclusion of medicaments or antimicrobial agents in the adhesive is also contemplated, as described in U.S. Pat. Nos. 4,310,509 and 4,323,557 both of which are hereby incorporated by reference in their entirety.

In some embodiments, the pressure sensitive adhesive layer can preferably transmit moisture vapor at a rate greater to or equal to that of human skin. While such a characteristic can be achieved through the selection of an appropriate adhesive, it is also contemplated herein that other methods of achieving a high relative rate of moisture vapor transmission may be used, such as pattern coating the adhesive on the backing, as described in U.S. Pat. No. 4,595,001, which is hereby incorporated by reference in its entirety.

Embodiments disclosed herein also provide methods of adjusting or selecting a peel force for a multi-layered assembly comprising a carrier having opposed sides; a heat sealable layer disposed on at least a portion of one of said sides of the carrier, said heat sealable layer comprising a partially salt neutralized ionomer; and a polymeric film comprising polyurethane and having opposed sides, wherein one of said sides of the polymeric film is in at least partial contact with said heat sealable layer. In some embodiments, the method comprises fabricating the assembly according to a method described herein. In some embodiments, the methods of selecting or adjusting a peel force comprises decreasing or increasing the percent salt neutralization of the ionomer. For example, as the percent salt neutralization is increased the peel force is decreased. According, the peel force can be selected or adjusted by increasing the percent salt neutralization to increase the peel force or the peel force can be selected or adjusted by decreasing the percent salt neutralization to decrease the peel force. The peel force can also be selected or adjusted by modifying the temperature to which the releasable layer is exposed to during the manufacturing process. For example, if the peel force is selected to be increased the temperature is increased. As the temperature is increased the peel force is increased. Accordingly, the assemblies described herein can be fabricated with a particular peel force by adjusting the percent salt neutralization and/or the temperatures described herein.

Release liners that are suitable for use in the multi-layered assemblies described herein can be made, e.g., of kraft papers, polyethylene, polypropylene, polyester or composites of any of these materials. The liners can also be coated with release agents, such as, e.g., fluorochemicals or silicones. For example, U.S. Pat. No. 4,472,480, the disclosure of which is hereby incorporated by reference in its entirety, describes low surface energy perfluorochemical liners. In some embodiments, the liners are papers, polyolefin films, or polyester films coated with silicone release materials. Examples of commercially available silicone coated release papers are, but not limited to, POLYSLIK silicone release papers available from James River Co., H. P. Smith Division (Bedford Park, Ill.) and silicone release papers supplied by Daubert Chemical Co. (Dixon, Ill.). In some embodiments, the liner is a super calendared Kraft paper with a water-based silicone release surface, such as, but not limited to, 1-60BKG-157 paper liner available from Daubert.

Other combinations of adhesives and liners can also be used in the embodiments disclosed herein. Those skilled in the art will be familiar with the processes of testing a new adhesive against different liners or a new liner against different adhesives to arrive at the combination of qualities desired in a final product. Additionally, in some embodiments, the choice of adhesives is limited to those that are safe to use on human skin, and can also be those that are of the class known as "hypoallergenic." The examples described herein, i.e., acrylate copolymers, are adhesives of this class.

In some embodiments, a carrier in a multi-layered assembly according to the present teachings, e.g., a multi-layered assembly used as a dressing, can be formed of a material that is substantially more rigid than the polymeric film used in the assembly, for example, to prevent the carrier from wrinkling during application. The carrier material should be heat-sealable to the film for the purpose of manufacturing the dressings. In some embodiments, the carrier materials include, but are not limited to, polyethylene/vinyl acetate copolymer-coated papers and polyester films. One non-limiting example of a carrier material is a polyethylene/vinyl acetate copolymer-coated super calendared Kraft paper (D78# BL SCK 11 OOPE Paper; Loprex LLC).

Non-limiting exemplary embodiments of multi-layered assemblies according to the present teachings are depicted in the Figures, which are discussed below. It is to be understood that the invention shall not be limited to the following illustrations and descriptions, but, rather, shall include any and all modifications and variations thereto as would occur to one of ordinary skill in the art.

Referring to FIGS. 1 and 1A, an exemplary multi-layered assembly 10 comprises a film 12, which is preferably conformable as described above. In an exemplary embodiment, film 12 comprises a polymeric film, and more especially, a polyurethane film, e.g., an aromatic polyether urethane film. The assembly further comprises a carrier 14 having a heat sealable layer 16 disposed on a bottom side thereof. In an exemplary embodiment, heat sealable layer 16 comprises a salt neutralized ionomer (e.g., ethylene acrylic acid) formed thereon. As discussed above, the salt neutralized ionomer can be applied to the bottom side of the carrier by utilizing a variety of techniques, e.g., as an emulsion coating, an extrusion coating, or an extruded layer. A top side 18 of carrier 14 may include a release agent in the form of, e.g., a release layer. In some embodiments, such a release layer may comprise a silicone polymer.

Figure 2:
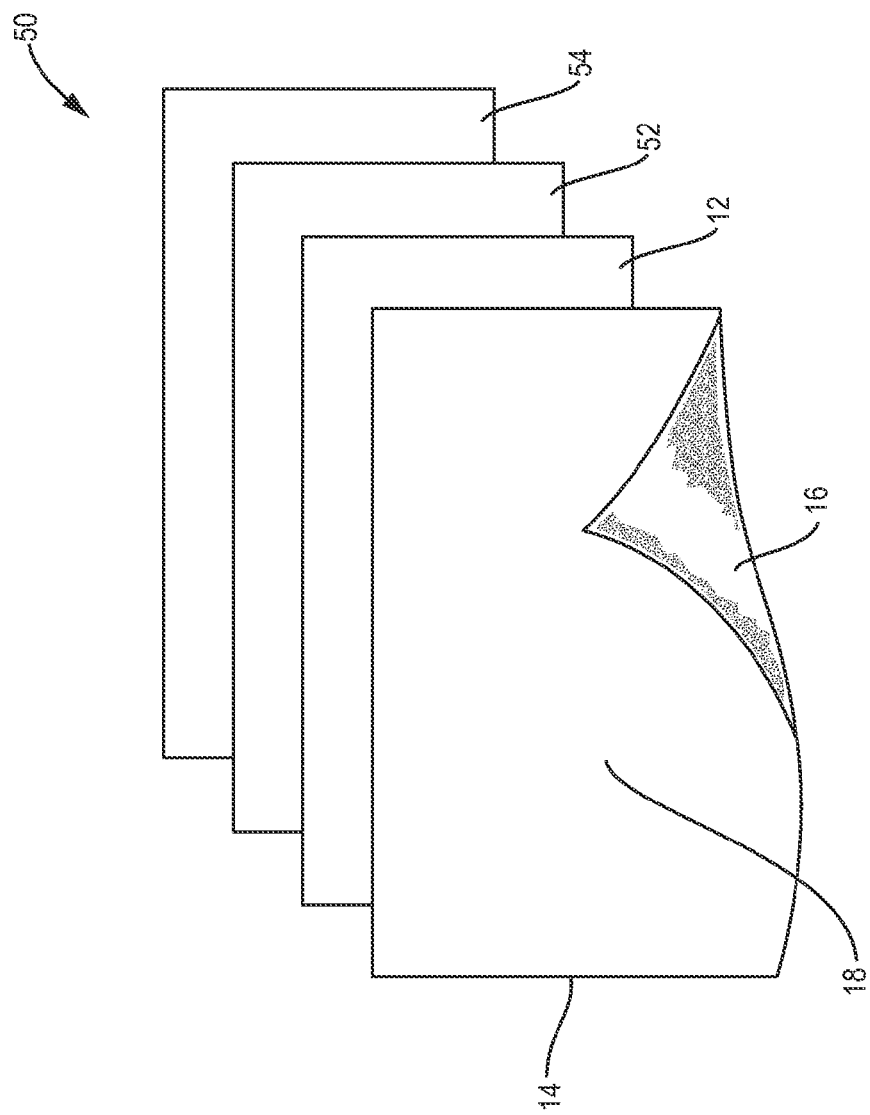
FIG. 2 is an example of a schematic depicting another exemplary multi-layered assembly.

In another embodiment schematically depicted in FIGS. 2 and 2A, a multi-layered assembly 50 is similar to multi-layered assembly 10 depicted in FIGS. 1 and 1A, and further comprises a pressure sensitive adhesive layer 52, and a protective release liner 54, which is positioned on pressure sensitive adhesive layer 52 opposite to film 12.

Figure 3:
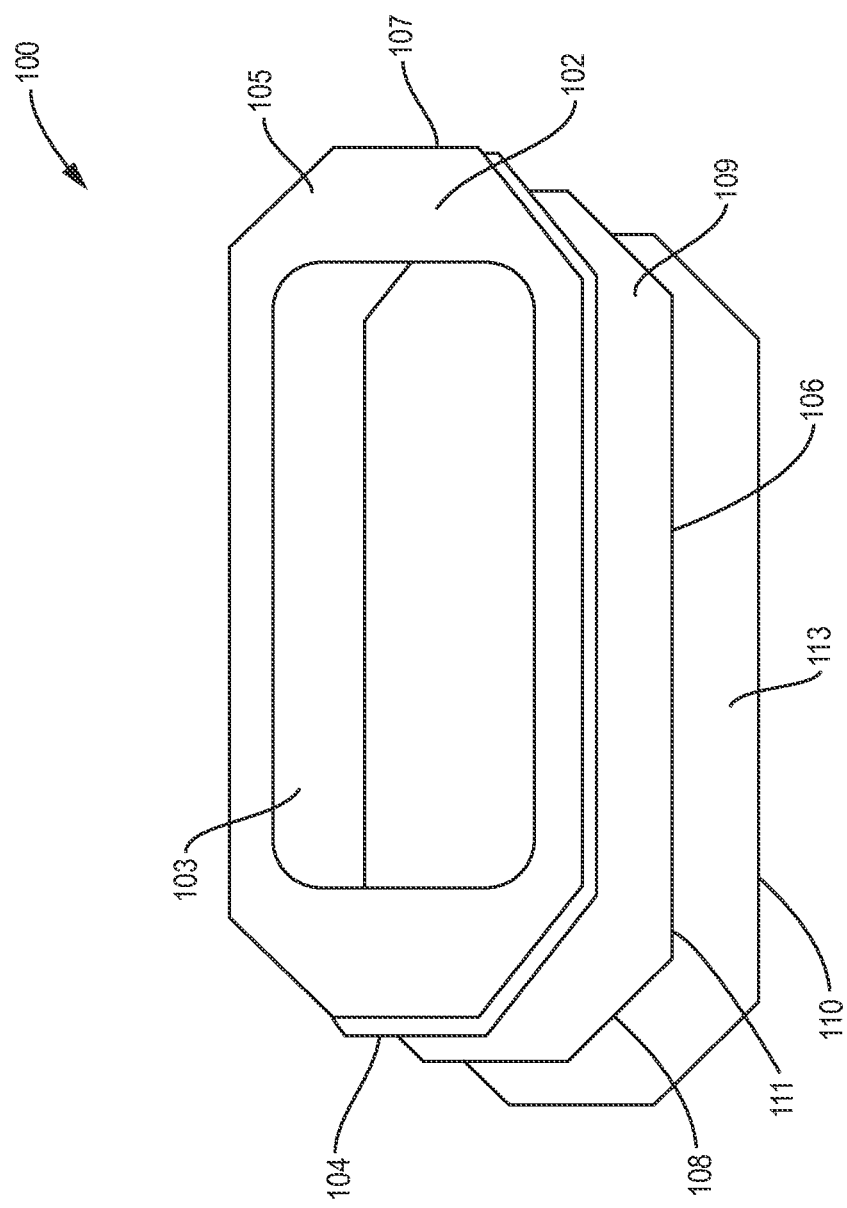
FIG. 3 is an example of a schematic depicting another exemplary multi-layered assembly.
Figure 3A:
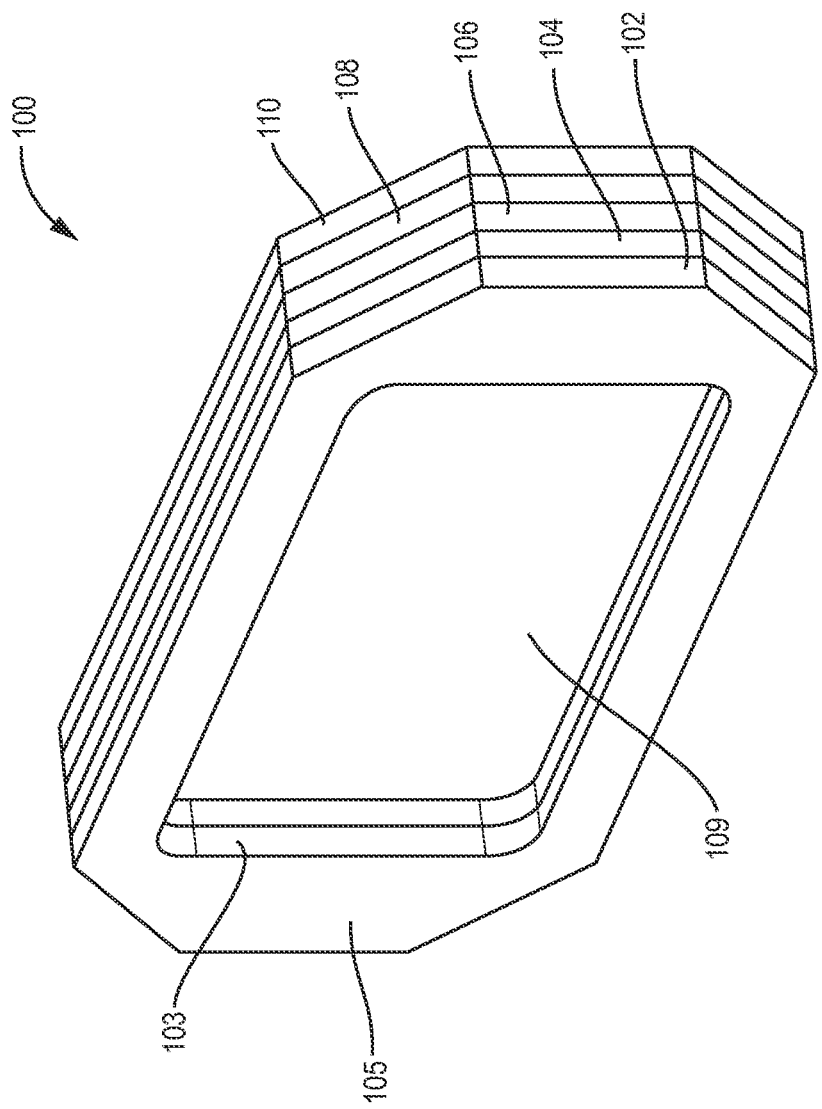
FIG. 3A is an example of a schematic depicting another exemplary multi-layered assembly.

Another exemplary embodiment of a multi-layered assembly 100 is depicted in FIGS. 3 and 3A. Here, multi-layered assembly 100 comprises a carrier 102 having a top side 105, which may have a release agent disposed thereon. The carrier 102 has a window 103 formed through a top side 105 and a bottom side 107 such that carrier 102 comprises a framed configuration. The multi-layered assembly 100 further comprises a heat sealable layer 104 disposed between the bottom side 107 of the carrier and a top side 109 of a conformable film 106, such as, a polyurethane film. The heat sealable layer 104 has a framed configuration that closely matches that of the carrier 102. Assembly 100 comprises a pressure sensitive adhesive layer 108 disposed between a bottom side 111 of the film 106 and a top side 113 of a protective release liner 110.

In some embodiments, any of the multi-layered assemblies described and/or contemplated herein may be in sheet or roll form. An exemplary multi-layered assembly and its method of manufacture are set forth in the following non-limiting and illustrative example. The Examples provided below are intended only for illustrative purposes.

EXAMPLE 1

An exemplary multi-layered assembly was formed by providing a 78 pound/ream super calendared kraft paper. The kraft paper was coated on one side with a platinum catalyzed DowCorning Syl-Off emulsion having a thickness of 0.5 pounds per 3,000 square feet ream to form a release layer, and the other side of the kraft paper was coated with a Michelman Michem Prime partialized sodium neutralized 498345N ethylene acrylic acid emulsion coating having a thickness of about 10 microns after drying as a non-permanent heat seal coating to form a heat sealable layer. Both coatings were done simultaneously on a gravure type coater and dried in a conventional oven. The dual coated paper was then wound in roll form and unwound onto a flat die cast extrusion line. The dual coated paper was fed across a roll stack positioned 3 inches to 5 inches from a slot die with the heat seal coating side up.

A 1.0 mil film of BASF SP-806 aromatic polyether urethane film, which was obtained from BASF corporation of New Jersey, U.S.A., was cast onto the paper carrier sheet with the melt temperature at the contact point of the paper being about 350 degrees Fahrenheit to facilitate a 190 gram per inch target peel strength. The film and paper carrier sheet were nipped together between a silicone rubber roll and a smooth steel roll at 500 psi. The urethane film with carrier was cooled as it moved along the roll stack to a winder where it was rolled into roll form.

The multi-layered assembly was stored at a simulated warehouse temperature of 120 degrees Fahrenheit for 24 hours and tested for peel values (test method ASTM 90 degree angle, 144 inch per second sled speed, 1 inch wide samples).

FIG. 4 depicts data obtained from the multi-layered assembly formed as discussed above. As shown in the table depicted in FIG. 4, the multi-layered assembly showed an average peel force of about 137 grams per inch over 2030 feet of the multi-layered assembly. FIG. 5 shows peel strength after 24 hours and exposure to a temperature of 120° F.

EXAMPLE 2

In order to provide a specific application requirement of 300 grams/inch of peel force (ASTM D3330-F), a 78 lb/ream super calendared kraft paper from Expera Specialty Papers, which was produced with a latex, clay and starch primed surface on both the A side and B side of the paper (commercially available), was coated on the B side with poly dimethyl silicone (platinum catalyzed). The heat sealable release coating was prepared by blending by weight 30% Michelman Michem Prime MP4983R acrylic acid emulsion, 33% Michelman Michem Prime MP49835N sodium neutralized acrylic acid emulsion and 37% water to achieve an acid to salt neutralization characterized by FTIR ratio of 13.3 to 1 for peak heights at 1700 cm$^{-1}$ to 1545 cm$^{-1}$ of the FTIR spectrum. The A side was then coated simultaneously as the B side coating to 8 microns thick sodium neutralized ethylene acrylic acid using a Myer rod coater and dried at 300° F.

A 4.5" 30:1 Gloucester extruder with an EDI 80" slot die was used to cast a 0.001" (1.0 mil) thick layer of BASF SP-806 aromatic polyether urethane resin onto the A side of the 78 lb/ream paper prepared as indicated. The urethane film was cast from the slot die at 0.050" thick and drawn down to 0.001" by a roll stack, which was also used to cool the film to ambient temperature. The urethane film was heated to between 410° F. to 430° F. and pressure was applied at the nip point between the steel roll and rubber roll of the roll stack at 700 psi. The temperature of the urethane film and roll stack along with an increase or decrease of the pressure was used to target the 300 grams/inch peel strength between the urethane and the heat sealable coating on the A side of the paper. The rubber roll used in the stack was made from a 60-62 Durometer silicone rubber, which had been ground to a smooth finish. The value of the peel force at the interface of the urethane and the heat sealable coating was adjusted by temperature, pressure and dwell time in the nip. Dwell time in the nip was about 0.15 seconds and is adjusted by the line speed.

The peel strength values were tested and compared to a 0.001" SP-806 aromatic polyether urethane film cast onto a 78 lb/ream super calendared kraft paper coated on the A side with a Michelman Michem Prime acrylic acid emulsion for peel consistency. Table 1 below lists the test results.

TABLE 1

| (40 data points) | SP-806 TPU to EAA Coated Paper | SP-806 TPU to Sodium Neutralized Coated Paper |
|---|---|---|
| Average Peel Force | 349 g/inch | 306 g/inch |
| Standard Deviation | 106.1 g/inch | 25.0 g/inch |
| 3x Stand. Dev/Average Peel | 91.1% | 24.5% |

EXAMPLE 3

A 1.5 mil ethylene methacrylic acid ionomer film and a 1.5 mil 9.7% acid ethylene acrylic acid film were obtained from New England Extrusion (Turners Falls, Mass.). The ethylene methacrylic acid ionomer film was produced from Dupont Surlyn 1605 sodium neutralized resin and the ethylene acrylic acid film was produced from Dow Primacor 1410 resin.

A Lubrizol 58245-031P aromatic polyether urethane resin was extruded to 1.0 mils thick extrudate on a Davis-Standard 4.5" 30:1 extruder with a 78" EDI slot die. The film was heat sealed by application of a 1" wide seal jaw to both the Primacor 1410 EAA film and the sodium neutralized Dupont 1605 Surlyn film with 1.5 second dwell time over a range of temperatures from 200° F. to 360° F. and seal pressures from 40 psi to 70 psi. The film laminates were then tested for peel strength using a TMI peel tester (ASTM D3330-F) to determine the robustness of the seal strength in order to determine the combination that had the widest seal window between 60 gram/inch to 300 gram/inch. The test results are shown below in Table 2.

TABLE 2

Sealed to 1.0 mil BASF SP-806 TPU Film

| Sample | Seal Temp (° F.) | 40 psi Peel Strength | 50 psi Peel Strength | 60 psi Peel Strength | 70 psi Peel Strength |
|---|---|---|---|---|---|
| Primacor 1410 | 200° | 4.25 | 7.44 | 9.55 | 6.42 |
| Primacor 1410 | 220° | 19.6 | 18.6 | 15.1 | 13.5 |
| Primacor 1410 | 240° | 26.7 | 32.2 | 53.6 | 46.4 |
| Primacor 1410 | 260° | 130 | 141 | 244 | 594 |
| Primacor 1410 | 280° | 503 | 779 | 709 | 890 |
| Primacor 1410 | 300° | 1167 | 1135 | 1304 | 1453 |
| Surlyn 1605 | 200° | 11 | 12.1 | 9.44 | 8.91 |
| Surlyn 1605 | 220° | 31.9 | 36.7 | 38.7 | 36 |
| Surlyn 1605 | 240° | 69.6 | 108 | 86.6 | 81.9 |
| Surlyn 1605 | 260° | 169 | 180 | 202 | 202 |
| Surlyn 1605 | 280° | 212 | 265 | 262 | 271 |
| Surlyn 1605 | 300° | 320 | 288 | 321 | 291 |

The sodium neutralized Surlyn 1605 sealed to 1.0 mil BASF SP-806 thermal plastic urethane (TPU) film showed a significantly improved seal range over the Primacor 1410 EAA film sealed to the SP-806 TPU film, thus allowing the seal range to be targeted more specifically.

EXAMPLE 4

All medical films, bandages, tools and surgical drapes need to be sterilized by some means in order to control hospital infections in patients. A common method is ethylene oxide gas sterilization where wound care products are placed in a closed chamber, heated up to 55 degrees C. and flooded with ethylene oxide gas for 3 to 6 hours. The combination of the high temperatures with a reactive gas have made it necessary for suppliers of current wound care bandages to limit sterilization or have the peel performance of the product be compromised. This can make it difficult for the health care provider to apply the wound care film to the wound as the peel strength increases making removal of the release paper difficult.

The unique interaction of the sealing surface of a salt neutralized ionomer laminated to urethane shows a significant improvement in both the peel strength retention and the consistency of the peel from one bandage to the next bandage after ethylene oxide sterilization as compared to the current standard products that are commercially available.

Wound care laminates were constructed by casting 0.001" thick SP-806 aromatic polyether urethane film onto a 78# super calendared kraft paper coated onto the lamination side (side A) of the paper with Michelman Michem Prime MP49835N sodium neutralized ethylene methacrylic acid emulsion with an acrylic acid to a salt neutralization ratio characterized by a ratio of 5.2 to 1 for the heights of the peaks at 1700 cm$^{-1}$ and 1545 cm$^{-1}$ in the FTIR spectrum of the salt partially neutralized ethylene methacrylate layer. The laminates were die cut to size. The peel strength was tested and found to be an average of 260 grams/inch. Commercial samples of 3M Tegaderm 9832F wound care dressing, which includes 0.9 mil aromatic urethane film laminated to a nominal 80 lb/ream paper coated on the lamination side with ethylene acrylic acid, were obtained with an initial peel strength of 394 grams/inch.

Figure 6A:
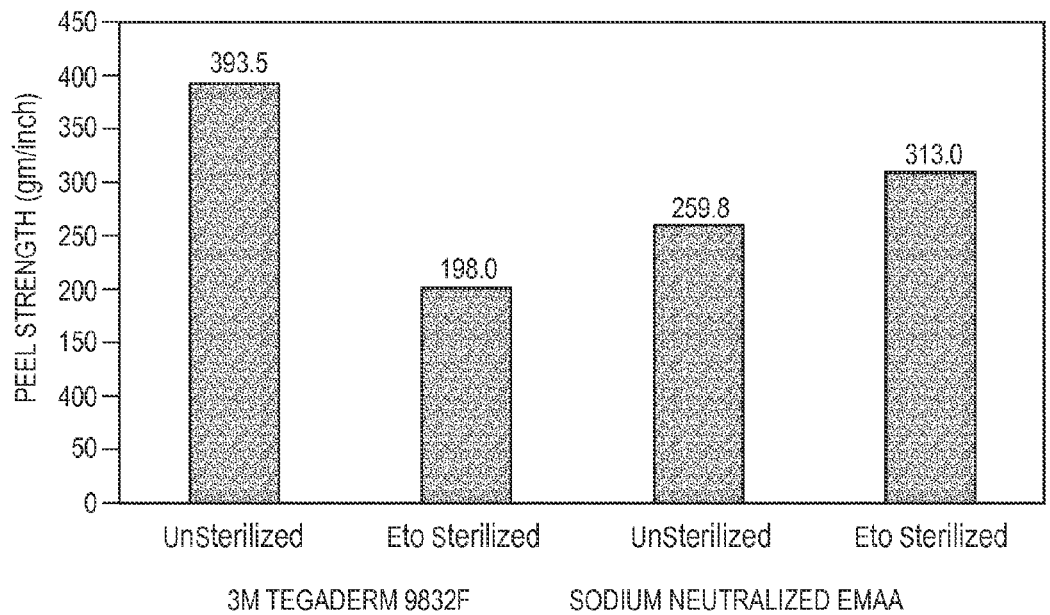
FIG. 6A depicts the effects of ethylene oxide sterilization on average peel strength.
Figure 6B:
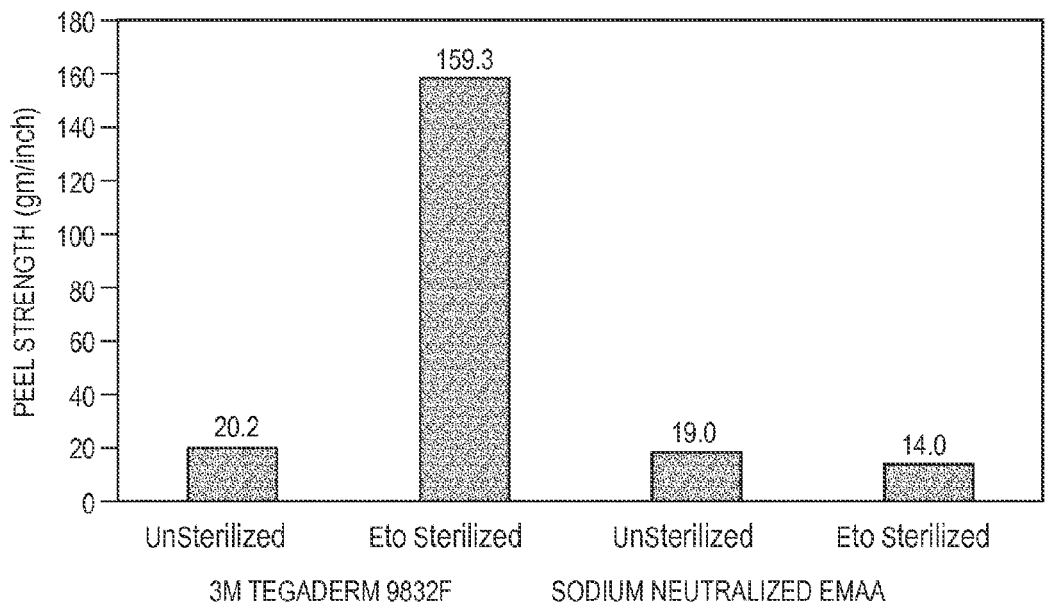
FIG. 6B depicts the effects of ethylene oxide sterilization on standard deviation of peel strength.
Figure 7A:
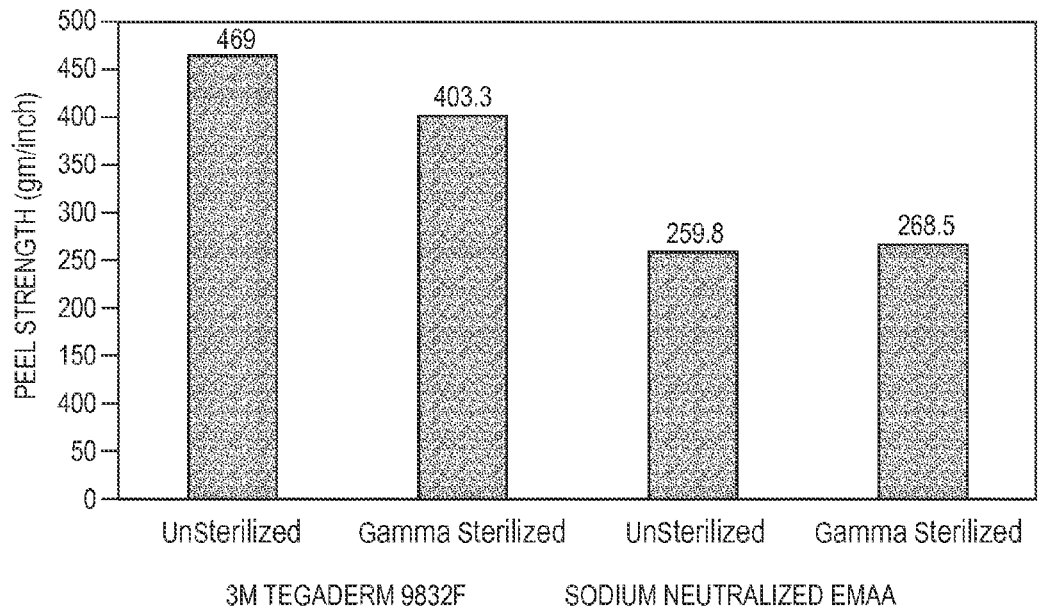
FIG. 7A depicts the effects of gamma irradiation on average peel strength.
Figure 7B:
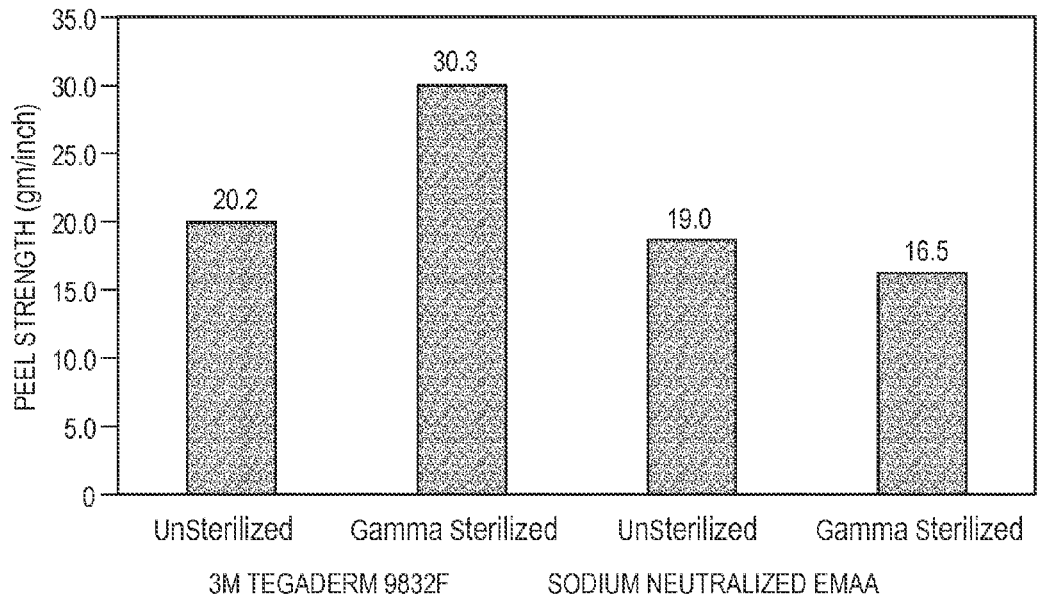
FIG. 7B depicts the effects of gamma irradiation on standard deviation of peel strength.

Samples of both materials were ethylene oxide sterilized by Anderson Scientific (ANSCI) at 54 degrees C. for 4 hours with 35.2 g (volume) of ethylene oxide gas. Samples were then retested for the peel strength and standard deviation of the peels. The 3M Tegaderm showed a 50% change in the peel strength and an increase in the standard deviation from 20 g/inch to 159 g/inch. The lamination made with the sodium neutralized ethylene acrylic acid coated paper to the SP-806 TPU showed a modest 21% change in peel strength and, significantly, the standard deviation decreased from 19 g/inch to 14 g/inch. FIGS. 6A and 6B illustrate the data obtained using ethylene oxide. Similar experiments were performed using gamma radiation sterilization and the results are summarized in FIGS. 7A and 7B.

Figure 8:
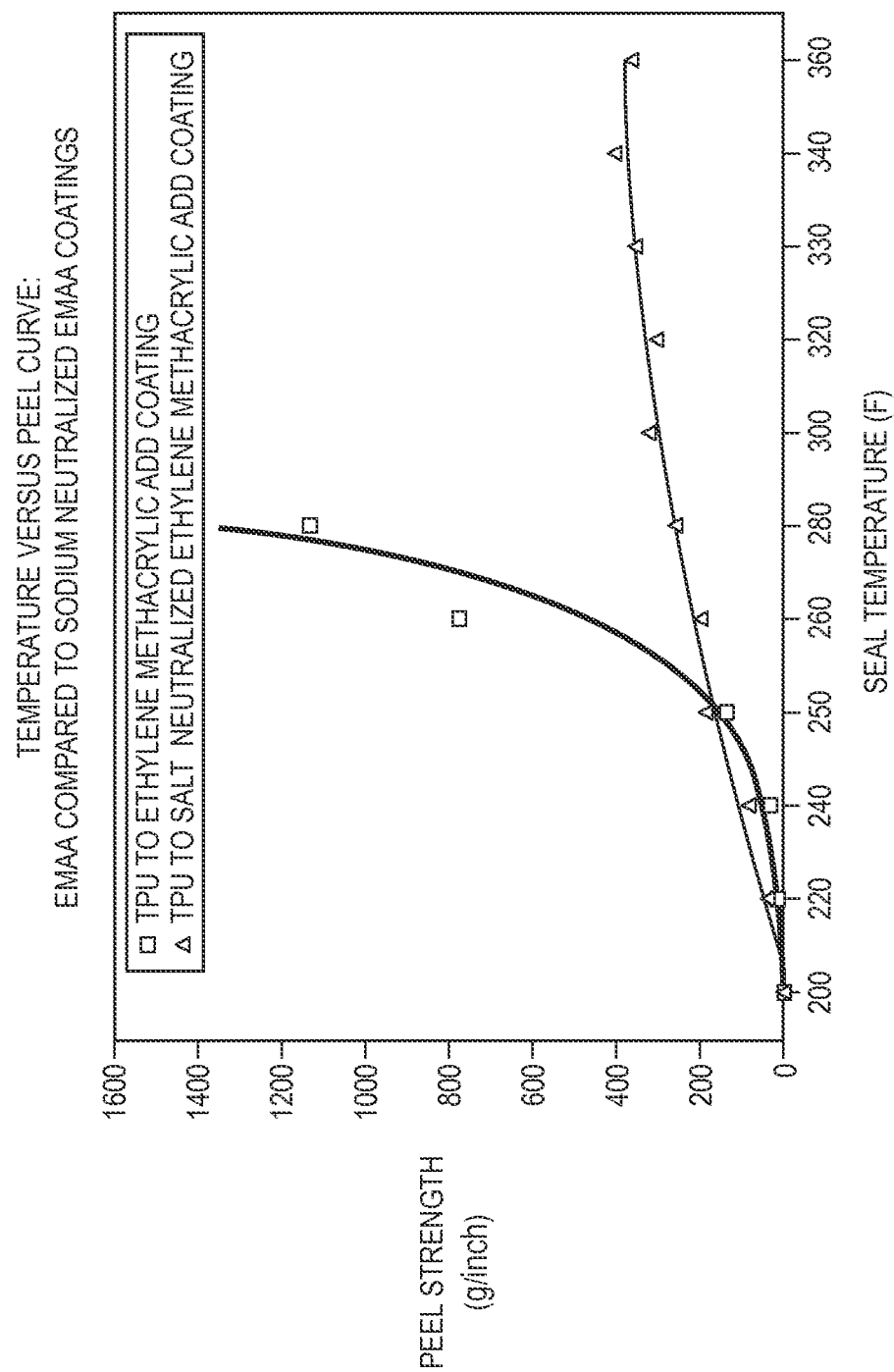
FIG. 8 depicts a temperature vs peel strength curve for different assemblies

FIG. 8 illustrates the effect of temperature on the peel strength of EMAA coatings compared to sodium neutralized EMAA coatings. As FIG. 8 shows as the seal temperature is increased the peel strength of the EMAA coating increases significantly and well above a lock seal. In contrast, the sodium neutralized EMAA coating peel strength does not exceed 400 g/inch even as the seal temperature is increased during manufacturing above 300° F.

In view of the foregoing description, it will be apparent that the embodiments are not limited to the specific details set forth herein and are for purposes of illustration, and that various other modifications are equivalent for the stated and illustrated functions without departing from the spirit and the scope thereof as defined in the appended claims.

What is claimed is:

1. A multi-layered assembly comprising:
a carrier having opposed sides;
a heat sealable layer disposed on at least a portion of one of said sides of the carrier, said heat sealable layer comprising a partially salt neutralized ionomer; wherein said partially salt neutralized ionomer comprises 100 percent of said heat sealable layer and
a polymeric film comprising polyurethane and having opposed sides, wherein one of said sides of the polymeric film is in at least partial contact with said heat sealable layer;
wherein the polymeric film is releasably sealed to said carrier via said heat sealable layer such that a 90-degree peel force in a range of about 50 grams/inch to about 600 grams/inch is required to release the polymeric film, and
wherein said polyurethane comprises any of an aromatic polyether urethane, an aliphatic polyether urethane, a poly (ether ester) block copolymer, or a poly (ether ester) block terpolymer.

2. The multi-layered assembly of claim 1, wherein said partially salt neutralized ionomer exhibits a salt neutralization level in a range of 5% to 70%.

3. The multi-layered assembly of claim 1, wherein said salt comprises any of a sodium, a potassium, a magnesium, a calcium, or a zinc salt.

4. The multi-layered assembly of claim 1, wherein said peel force varies by less than 25% when said assembly is exposed to a temperature of about 50° C. for 24 hours.

5. The multi-layered assembly of claim 1,
wherein said peel force varies by less than 25% after said assembly is subjected to ethylene oxide sterilization or by less than 10% after said assembly is subjected to gamma ray sterilization.

6. The multi-layered assembly of claim 1, wherein said partially salt neutralized ionomer comprises a partially salt neutralized ethylene acrylic acid copolymer.

7. The multi-layered assembly of claim 6, wherein said partially salt neutralized ethylene- acrylic acid copolymer exhibits a salt neutralization level in range of 5% to 70%.

8. The multi-layered assembly of claim 1, wherein the polymeric film comprises a pressure sensitive adhesive layer disposed on a side thereof opposed to the side that is in at least partial contact with said heat sealable layer.

9. The multi-layered assembly of claim 8, further comprising a protective release liner disposed on the pressure sensitive adhesive layer.

10. The multi-layered assembly of claim 8, wherein said heat sealable layer exhibits an FTIR spectrum exhibiting a peak at about 1700 cm$^{-1}$ and a peak in the range of about 1500 to about 1560 cm$^{-1}$.

11. The multi-layered assembly of claim 10, wherein a ratio of the height of the peak at about 1700 cm$^{-1}$ to the height of the peak in the range of about 1500 to about 1560 cm$^{-1}$ is in a range from about 20 to about 0.5.

12. A collection of multi-layered assemblies, comprising
a plurality of multi-layered assemblies each of which comprises a carrier having opposed sides,
a heat sealable layer disposed on at least a portion of one of said sides of the carrier, said heat sealable layer comprising a partially salt neutralized ionomer, wherein said partially salt neutralized ionomer comprises 100% of said heat sealable layer, and
a polymeric film comprising polyurethane and having opposed sides, wherein one of said sides of the polymeric film is in at least partial contact with said heat sealable layer,
wherein the polymeric film is releasably sealed to said carrier via said heat sealable layer such that a 90-degree peel force in a range of about 50 grams/inch to about 600 grams/inch is required to release the polymeric film,
wherein said polyurethane comprises any of an aromatic polyether urethane, an aliphatic polyether urethane, a poly (ether ester) block copolymer, or a poly (ether ester) block terpolymer; and
wherein the variation in peel force among said assemblies as measured by 3 times the standard deviation as a percent of the average peel force is less than 30%.

13. A multi-layered assembly comprising:
a carrier having opposed sides,
a heat sealable layer disposed on at least a portion of one of said sides of the carrier, said heat sealable layer comprising a partially salt neutralized ionomer, wherein said partially salt neutralized ionomer comprises 100% of said heat sealable layer,
a polymeric film comprising a polyurethane and having opposed sides, wherein one of said sides of the polymeric film is in at least partial contact with said heat sealable layer,
wherein said polyurethane comprises any of an aromatic polyether urethane, an aliphatic polyether urethane, a poly (ether ester) block copolymer, or a poly (ether ester) block terpolymer;
wherein said polymeric film is releasably sealed to said carrier via said heat sealable layer such that a peel force in a range of about 50 grams/inch to about 600 grams/ inch is required to release the polymeric film, and
wherein said peel force varies by less than 50 g/inch when said assembly is exposed to a temperature of 50° C. for up to 24 hours.

14. The multi-layered assembly of claim 13, wherein said peel force is in a range of about 200 grams/inch to about 500 grams/inch.

15. A multi-layered assembly comprising:
a carrier having opposed sides;
a heat sealable layer disposed on at least a portion of one of said sides of the carrier, said heat sealable layer comprising a partially salt neutralized ionomer, wherein said partially salt neutralized ionomer comprises 100% of said heat sealable layer, and
a polymeric film comprising polyurethane and having opposed sides, wherein one of said sides of the polymeric film is in at least partial contact with said heat sealable layer,
wherein said polyurethane comprises any of an aromatic polyether urethane, an aliphatic polyether urethane, a poly (ether ester) block copolymer, or a poly (ether ester) block terpolymer; and
wherein said polymeric film is releasably sealed to said carrier via said heat sealable layer such that a peel force required to release the polymeric film remains below about 400 grams/inch as temperature of the assembly is maintained at 50 degrees C. for 24 hours.

16. The multi-layered assembly of claim 15, wherein said partially salt neutralized ionomer comprises a partially salt neutralized ethylene acrylic acid copolymer.

17. A multi-layered assembly comprising:
a carrier having opposed sides;
a heat sealable layer disposed on at least a portion of one of said sides of the carrier, said heat sealable layer comprising a partially salt neutralized ionomer; and
a polymeric film comprising polyurethane and having opposed sides, wherein one of said sides of the polymeric film is in at least partial contact with said heat sealable layer;
wherein the polymeric film is releasably sealed to said carrier via said heat sealable layer such that a 90-degree peel force in a range of about 50 grams/inch to about 600 grams/inch is required to release the polymeric film, and
wherein said polyurethane comprises any of an aliphatic polyether urethane, a poly (ether ester) block copolymer, or a poly (ether ester) block terpolymer.

* * * * *

UNITED STATES PATENT AND TRADEMARK OFFICE
CERTIFICATE OF CORRECTION

PATENT NO. : 9,895,862 B2  
APPLICATION NO. : 14/265051  
DATED : February 20, 2018  
INVENTOR(S) : Thomas C. Burke et al.

Page 1 of 1

It is certified that error appears in the above-identified patent and that said Letters Patent is hereby corrected as shown below:

On the Title Page

Item [73], Assignee name should read:  
--[73] Assignee: Argotec LLC--

Signed and Sealed this  
Twenty-seventh Day of November, 2018

Andrei Iancu  
*Director of the United States Patent and Trademark Office*